United States Patent [19]

Gaspar et al.

[11] 4,066,899

[45] Jan. 3, 1978

[54] UNDERWATER RADIOGRAPHIC SYSTEM

[76] Inventors: Randle Gaspar, Rte. 2, Box 7; Claud A. Burk, Rte. 2, Box 43 B, both of Luling, La. 70070

[21] Appl. No.: 722,570

[22] Filed: Sept. 13, 1976

[51] Int. Cl.$^2$ .................... G01N 23/00; G03B 41/16
[52] U.S. Cl. ............................. 250/358 P; 250/321
[58] Field of Search ............... 250/320, 321, 358 P

[56] References Cited

U.S. PATENT DOCUMENTS

| 2,478,842 | 8/1949 | Schwartz et al. | 250/358 P |
| 3,666,944 | 5/1972 | Baldinger | 250/321 |

Primary Examiner—Alfred E. Smith
Assistant Examiner—T. N. Grigsby
Attorney, Agent, or Firm—Pugh & Keaty, Ltd.

[57] ABSTRACT

An apparatus for making radiographic pictures of an object submerged in a liquid comprising a substantially watertight housing having a reduced central section provided with a liquid displacing seal. The object to be irradiated is receivable in the reduced central section adjacent the liquid displacing seal. An irradiating camera is rigidly mounted in the housing. A sensitized film is additionally placed in the housing, oriented to receive radiation from the radiation camera after it irradiates the submerged object. In the preferred embodiment the reduced central section is a semicircular notch permitting irradiation of a partial section of the submerged object (see FIG. 1). An alternative embodiment has a hinged circular reduced central section permitting irradiation of an entire cross section of the submerged object to be irradiated. The apparatus can be transported underwater, mounted and actuated by a single operator.

10 Claims, 5 Drawing Figures

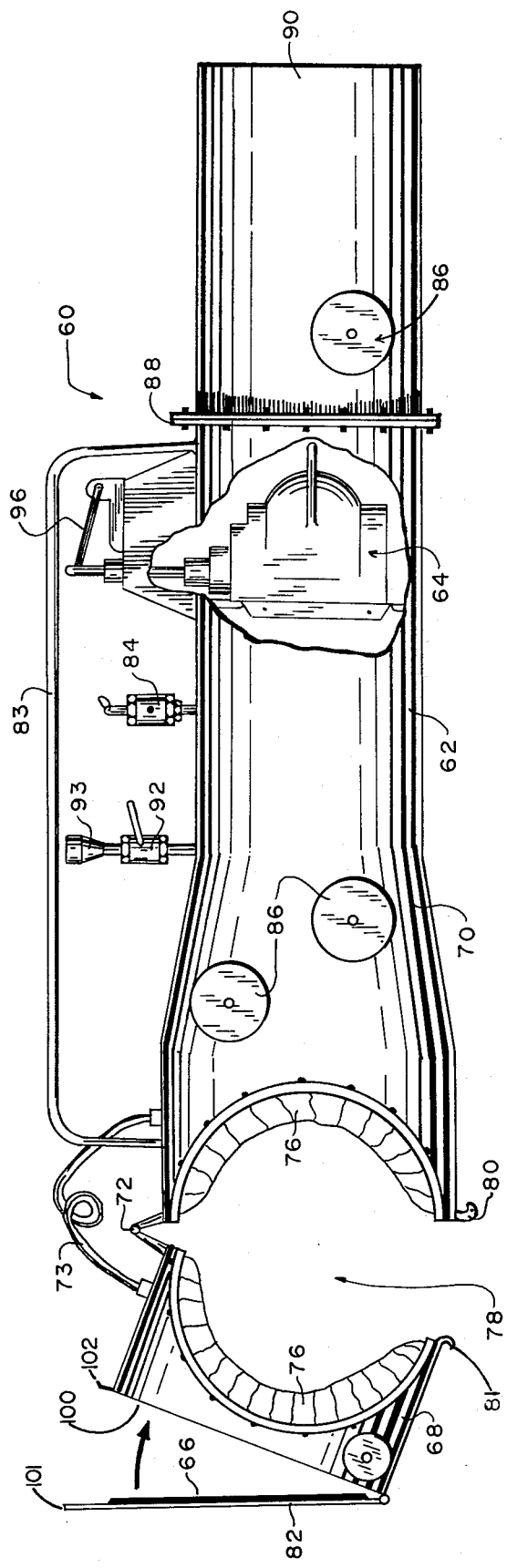
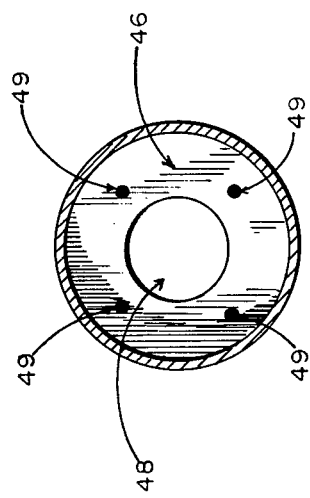
FIG. 4.
FIG. 5.

UNDERWATER RADIOGRAPHIC SYSTEM

BACKGROUND OF THE INVENTION

1. Field of the Invention

The present invention relates to radiographic pictures, commonly referred to as "X-rays." More particularly, the present invention relates to an apparatus for making radiographic pictures of objects submerged in an underwater environment.

2. Prior Art

Undersea exploration and industry have created extensive constructions on our ocean floors. This is particularly true in the oil and gas industry where thousands of miles of various sizes and types of piplelines have been laid for the transmission of petroleum products. Additionally, massive drilling and production facilities, called "oil platforms" or "oil rigs" have been constructed, often many miles offshore in deep water. These platforms derive their support and strength from complex foundations, having multiple structural parts and members, called "jackets," which are anchored to the ocean floor with piling or the like.

While these examples of undersea constructions may be well designed and constructed initially, they are subsequently subjected to abusive forces, such as salt water corrosion, chemical attack, and swift underwater currents. Intense weather conditions such as hurricanes periodically occur which can destroy equipment, particularly that which is not properly maintained. Therefore, a great need exists for a device which can quickly and effectively examine underwater objects in place such as pipelines, oil rig jackets, drilling platforms, piling and the like to deterime their structural integrity. Visual inspection is ineffective where structural parts, or welds may have fractures which are too small, subsurface of coated with marine growth.

Radiography, because of its ability to make photographs of solid material density, has been extensively used in examination of several types of structural members and like objects. Radiography is well suited for examining structures such as pipelines, welds, piling or girders. While radiographs are well suited and extensively used to examine solid structureal members, there is a need for an economical, simple, and effective apparatus for making radiographic pictures in an underwater environment.

Two prior art devices for underwater radiography are disclosed in U.S. Pat. No. 3,891,845, issued June 24, 1975 to Paul N. English; and U.S. Pat. No. 3,673,407, issued June 27, 1972 to George C. Wiswell.

Generally, the prior art devices have failed to solve the problem of underwater radiography staisfactorily. Prior art devices are generally complex and awkward to handle. Since underwater radiography devices are generally handled and operated by a diver, there is a need for ease of operation and ease of transportation. Radiography demands that water be void from the area traversed by the radiation beam and that there be no significant backscattering caused by the water. The presence of water in the beam transmission are distorts the radiographic pictures by causing attenuation of the radiation beam. An additional problem in underwater radiography is orientation of the radiation beam, the object to be radiographed, and the sensitized film from which are produced the final radiographies. Some prior art devices require that the diver position and orient the film and radiation beam around the object while underwater. This method is time consuming and therefore costly. It also requires additional skill and training in the diver.

3. General Discussion of the Present Invention

The device of the present invention solves these prior art problems by providing a watertight, self contained, fully equipped and oriented underwater radiography device.

It is an object of the present invention to provide an apparatus for underwater radiography which enables the user to quickly and efficiently take underwater radiographs of desired objects. It is a further object of the present invention to provide a device for making underwater radiographs without requiring extensive operation by the user to remove water from the radiation beam transmission area. It is still a further object to insure that no significant backscattering occur due to the presence of water in proximity to the backside of the radiographic source.

BRIEF DESCRIPTION OF THE DRAWINGS

For a further understanding of the nature and objects of the present invention, reference should be had to the following detailed description of the drawings, in which like parts are given like reference numerals, and wherein:

FIG. 4 is a side view, partially cut away, of a second basic embodiment of the present invention;

FIG. 5 is a frontal view of the bulkhead structure of the present invention.

DETAILED DESCRIPTION OF THE PREFERRED EMBODIMENTS

Figure 1:
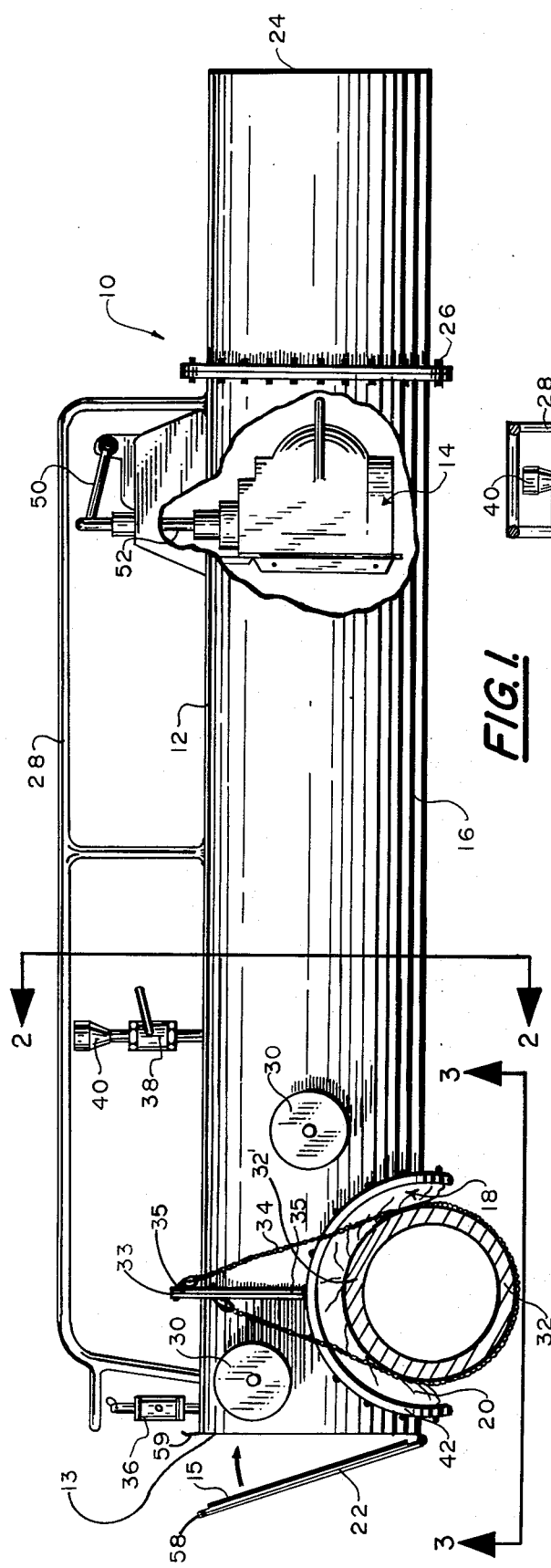
FIG. 1 is a side view, partially out away, of the preferred embodiment of the apparatus of the present invention positioned on a hollow metal pipe.
Figure 2:
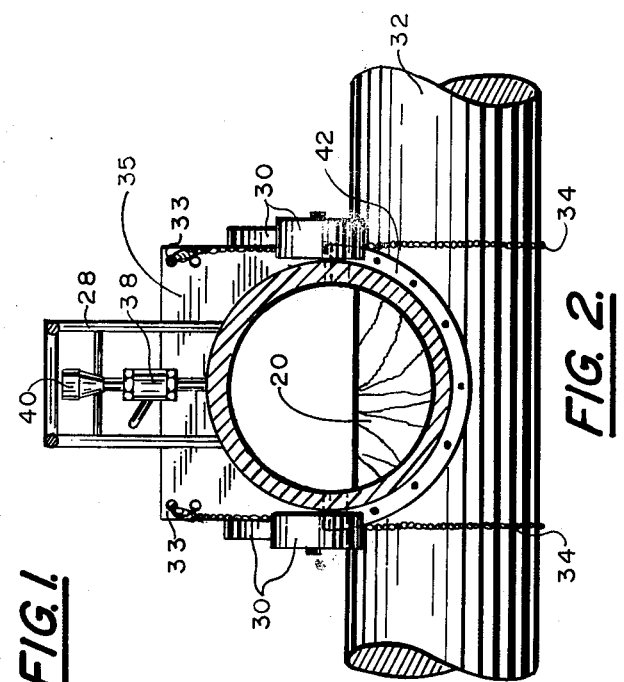
FIG. 2 is a sectional view taken through section lines 2—2 of FIG. 1.
Figure 3:
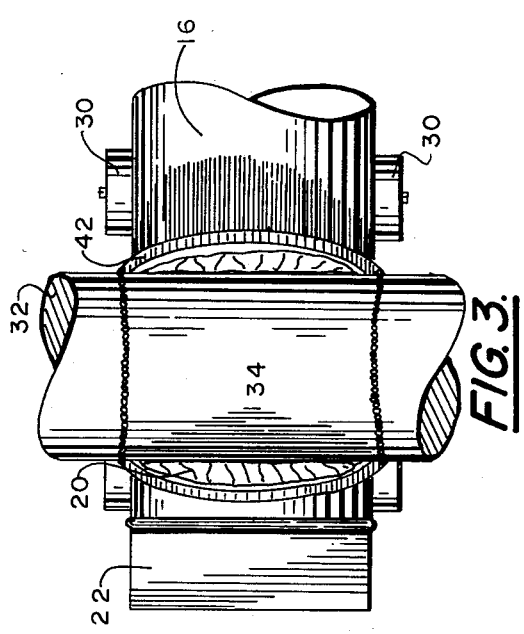
FIG. 3 is a partial view taken from the perspective of lines 3—3 of FIG. 1.

With particular reference to FIGS. 1, 2 and 3, the preferred embobiment of the underwater radiography apparatus of the present invention, designated generally by the numeral 10, is comprised of three basic elements: a watertight housing 12, irradiating means 14, and film means 15.

As can best be seen in FIG. 2, housing 12 features an elongated, preferably cylindrical hollow tube 16 having a recessed lateral saddle 18 which is covered with a flexible neoprene seal 20. Flange 42 forms a substantially watertight seal between tube 16 and neoprene seal 20.

Film holding plate 22 is hingedly attached to one extreme end portion of housing 12. The inner surface of film holding plate 22 is coated with, for example, quarter inch neoprene, providing a substantially watertight seal with tube end cover 13 when plate 22 is locked using latches 58, 59 in a closed position.

End cover 13 is, for example, a circular aluminum plate welded to the end portion of tube 16, making a watertight seal.

Air extension sub 24 is sealably attached to the rear end of tube 16 at entry flange 26. The rear sub extention 24 serves to keep water away from the back-side of the irridating x-ray source 14 to prevent or substantially eliminate any potential back-scattering of the x-rays by the water.

For ease of handling, housing 12 is provided with hand rail 28 rigidly affixed to housing 12 at tube 16. Balancing weights 30 are rigidly affixed to the outer surface of tube 16 to achieve neutral buoyancy of the underwater radiography apparatus 10.

As can be seen best in FIG. 1, housing 12 is attachable at lateral saddle 18 to object 32 using spring tension chains 34.

Removal of highly excessive pressure from housing 12 is automatically provided by pop off valve 36 affixed to tube 16 (see FIG. 2). Air valve 38, which can be for example a quarter inch valve, is affixed to housing 12. Quick disconnect fitting 40 is attached to the outlet of air valve 38.

In the preferred embodiment, housing 12 can be constructed of, for example, eight inch diameter aluminum pipe having a preferred overall length of approximately 44 inches. Recessed saddle 18 is generally semicircular in shape, having an exemplary radius of four and a half inches. The center of recessed saddle 18 can be, for example, six inches from the end of housing 12 to which the film holding plate 22 is attached. Neoprene seal, for example, quarter inch thick, is fixedly attached to housing 12 using aluminum flanges 42 and bolts having an exemplary one inch spacing.

Handling rail 28, exemplarily constructed of three-eighths inch aluminum bar, is rigidly affixed to housing 12 using conventional means such as welding or the like. Spring tensioned chains 34 are anchored to bracket 35. Bracket 35 is preferably aluminum and attached to tube 16 approximately perpendicular to the central axis of housing 12 at a distance of for example six inches from the end of tube 16 which has film holding plate 22. Bracket 35 is on the upper surface of housing 12, opposite saddle 18. Bracker 35 shich can be rectangular as shown in FIG. 2, or curcular, is provided with a plurality of holes 33 for anchoring either end of chains 34.

A bulkhead 46, preferably circular, is rigidly mounted in housing 12 by welding or like conventional methods. As can best be seen by FIG. 5, bulkhead 46 is provided with a central opening 48 which allows radiation from irradiating means 14 to pass through bulkhead 46. The face of bulkhead 46 is preferably perpendicular to the central axis of housing 12. Bulkhead 46 can be spaced for example a distance of thirty-six inches from film holding plate 22. Desired taps 49 can be provided for anchoring the irradiating means 14 to the bulkhead 46.

Irradiating means 14 is preferably a conventional X-ray camera, which is rigidly mounted inside housing 12 to bulkhead 46. The proper orientation of irradiating means 14, film 15 and the object to be radiographed are permanently set by their respective positions in the housing. Irradiating means 14 has its beam pointed at film 15, but the beam traverses recessed saddle 18. It can be seen by one skilled in the art that the upper portion 32' of the object secured in recessed saddle 18 will be radiographed by irradiating camera means 14, and the film 15 will form a radiographic picture thereof.

Actuating switch 50 for the X-ray source (normally kept sealed) is externally mounted on tube 16. Switch 50 is provided with probe 52 which is slidably mounted through tube 16 to the X-ray source located within the irradiating means 14.

Film 15 is preferably conventional radiography film and is mounted on film holding plate 22.

A second embodiment of the present invention is illustrated in FIG. 4. As can be seen best by FIG. 4, the underwater radiation device, designated generally by the numeral 60, is comprised of housing 62, film irradiating means 64 and film means 66. Housing 62, preferably cylindrical, is comprised of film section 68 and camera section 70 which are pivotally connected at hinge 72. Flexible hose 73 pneumatically connects film section 68 and the camera section 70, the facing ends of which are closed and lined with water displacing neoprene seals 76. This configuration provides a cylindrical, object-holding, lateral saddle 78 when film section 68 is rotated about hinge 72 to a closed position and latches 80, 81 are locked.

Film section 68 has film hatch 82 hingedly fixed to the outermost face of film section 68. Film hatch 82 contacts end plate 100 when it is closed by engaging latches 101, 102. End plate 100 is preferably welded to the end portion of film section 68, making a watertight seal. Housing 62 is further provided with handling rail 83, pop off valve 84 for releasing greatly excessive pressures, weights 86 for controlling the buoyancy of housing 62, and entry flange 88 for internal access to housing 62.

Air extension sub 90 is affixed to housing 62 at entry flange 88 using conventional means such as bolting or the like. Air extension sub 24 is provided to prevent backscattering of irradiation from irradiating means 14. The increased void created by air extension sub 24 provides an area for transmission of stray radiation rays emitted by irradiating means 14. Air extension sub 24 can be for example constructed of eight inch diameter aluminum pipe with an exemplary length of eighteen inches. Air valve 92, which is rigidly connected to housing 62, provides an inlet valve thereto, and is provided with a quick disconnect fitting 93.

The inner portion of housing 62 rigidly holds irradiating means 64, which is oriented to direct its beam at film 66. Actuating switch 96 is slidably mounted through camera section 70 of housing 62 to irradiating means 64.

OPERATION

The apparatus of the preferred embodiment is a totally complete unit, requiring a minimum of operations by the used to function. A diver carries the apparatus easily by hand rails 28 to a desired object to be radiographed. The object is placed adjacent housing 12 at recessed saddle 18. Neoprene seal 20 assures a watertight seal around the portion of the object to be radioraphed. Spring tension chains 34 are wrapped around the object and anchored in holes 33 of bracket 35. This rigidly positions the apparatus as is required for the radiographic picture to be made.

The diver then triggers irradiating means 14 by pulling actuating switch 50. Radiation bombards sequently the upper portion of the object and then the film 15, thus, with the preferred embodiment of FIGS. 1, a partial section of the desired object is irradiated. To obtain a picture of the entire section of the object, the underwater radiographic device 10 is rotated a number of degrees (e.g. 90°) after each "shot" until all four portions and hence the entire object section if radiographed. The diver carries film as needed in plastic watertight bags, substituting new film for used film after each shot. The first embodiment is particularly useful for x-raying hollow objects such as for example metal pipes.

In the second embodiment of the present invention, a diver in like fashing carries the apparatus to the desired object easily using hand rail 83. The object to be radiographed is sandwiched between film section 68 and camera section 70 and held in object holding saddle 78. Latches 80, 81 rigidly secure the device. The diver triggers actuating switch 96 to release a radiation beam from irradiating camera means 64 which bombards the object to be radiographed and film 66, thereby forming the conventional radiographic picture. The second embodiment is particularly useful for x-raying solid objects, such as for example wood pilings.

The second embodiments, because of the larger area of saddle 78, can irradiate a full section of the object, thus only one shot is necessary to radiograph the entire object section.

An air supply can be connected to air inlet valve 38 using quick release fitting 40. If necessary, air can be injected into housing 12 to expand neoprene seal 18 as necessary to insure a watertight fit of neoprene 18 around object 32. Likewise, in the second embodiment, air inlet valve 92 can be used to expand the neoprene seals 76 to insure a watertight fit of the device 60 on the object. It should be understood that the devices 10, 60 are internally water free at all times and that the air inlet valves 38,92 are only used to expand the neoprene seals 20, 76.

As a further preventive of back or side scattering, the interiors of the preferred embodiments can be lined with lead. Additionally, for better resolution of the X-ray pictures, the film sections of the embodiments could be shortened so as to place the films as close to the objects being radiographed as possible. Likewise, depending on the diameter of the pipes being radiographed by the first embodiment, the spacing of the source 14 to the object 32 could be made greated in proportion to the object diameter. An ideal ratio of spacing to diameter is thought to be approximately seven-to-one. These are only exemplary of the many possible variations.

Because many varying and different embodiments may be taught within the scope of the inventive concept herein taught and because many modifications may be made in the embodiments herein detailed in accordance with the descriptive requirements of the law, it should be understood that the details herein are to be interpreted as illustrative and not in a limiting sense.

What is claimed as invention is:

1. An apparatus for making radiographic pictures of an object submerged in a liquid, comprising:
   a. a substantially watertight elongated housing, said housing being provided with a lateral, recessed saddle, said housing being attachable to said object at said recessed saddle;
   b. camera means for irradiating said object with a beam of X-rays, said camera means being encased and rigidly supported within said watertight housing, said camera means positioned at a point in said housing substantially removed from said recessed saddle in the longitudinal direction; and
   c. sensitized film means for making radiographs encased in said housing at the opposite end portion of said housing from said camera means, said film means oriented so that at least a portion of said recessed section is between said radiation means and said film means.

2. The apparatus as defined in claim 1, further comprising a trigger means on the exterior of said housing for actuating said camera means.

3. The apparatus as defined in claim 2, further comprising valve means on said housing for releasing excess pressure from said watertight housing.

4. The apparatus as defined in claim 3, further comprising weight means removably located on the exterior of said housing for giving said housing a desired neutral buoyancy.

5. The apparatus of claim 1, wherein said watertight housing is hinged at said recessed saddle, and said saddle is substantially circular.

6. The apparatus of claim 1 wherein said housing is provided with a film loading hatch.

7. The apparatus of claim 1 wherein said recessed saddle comprises a semicircular reduced central saddle lined with a flexible seal.

8. The apparatus of claim 1 wherein said camera means is located within said housing at a substantial distance away from said recessed saddle and from the opposite end of said housing, whereby no water is present in close proximity to the rear of said camera means.

9. A method for making radiographic pictures in an underwater environment, which comprises the steps of:
   a. providing a substantially watertight underwater radiographic device, which device comprises:
      i. a substantially watertight elongated housing, said housing being provided with a lateral, recessed saddle, said housing being attachable to said object at said recessed saddle;
      ii. camera means for irradiating said object with a beam of X-rays, said camera means being encased and rigidly supported within said watertight housing, said camera means positioned at a point in said housing substantially removed from said recessed saddle in the longitudinal direction; and
      iii. sensitized film means for making radiographs encased in said housing at the opposite end portion of said housing from said camera means, said film means oriented so that at least a portion of said recessed section is between said radiation means and said film means.
   b. removing water from the radiographic device;
   c. attaching the radiographic device at the recessed saddle to an object to be irradiated; and
   d. irradiating the object with a radiation beam from the camera means.

10. The method as described in claim 9, wherein the lateral recessed saddle of said watertight housing comprises a semicircular reduced central saddle linked with a flexible seal, and there is further provided the additional step of adding air to the watertight housing to inflate the flexible seal of the central saddle, thereby obtaining a watertight seal between the central saddle and the object to be irradiated.

* * * * *